(12) United States Patent
Abal et al.

(10) Patent No.: US 12,415,033 B2
(45) Date of Patent: Sep. 16, 2025

(54) REAL TIME DRIP CHAMBER MONITOR

(71) Applicant: CareFusion 303, Inc., San Diego, CA (US)

(72) Inventors: Daniel M. Abal, San Diego, CA (US); Brendan Burgess, Poway, CA (US); Ramkumar Subramanian, San Diego, CA (US); Michael Zirkle, Carlsbad, CA (US)

(73) Assignee: CAREFUSION 303, INC., San Diego, CA (US)

( * ) Notice: Subject to any disclaimer, the term of this patent is extended or adjusted under 35 U.S.C. 154(b) by 1158 days.

(21) Appl. No.: 17/235,724

(22) Filed: Apr. 20, 2021

(65) Prior Publication Data

US 2021/0369959 A1    Dec. 2, 2021

Related U.S. Application Data

(60) Provisional application No. 63/030,817, filed on May 27, 2020.

(51) Int. Cl.
*A61M 5/168* (2006.01)
*A61M 5/14* (2006.01)
*A61M 5/142* (2006.01)

(52) U.S. Cl.
CPC .......... *A61M 5/1689* (2013.01); *A61M 5/142* (2013.01); *A61M 5/16831* (2013.01);
(Continued)

(58) Field of Classification Search
CPC ................ A61M 5/1689; A61M 5/142; A61M 5/16831; A61M 2205/3379;
(Continued)

(56) References Cited

U.S. PATENT DOCUMENTS

2013/0201482 A1\* 8/2013 Munro ................... G01N 21/27
356/407
2017/0189613 A1 7/2017 Hungerford et al.
(Continued)

FOREIGN PATENT DOCUMENTS

EP    2380612 A    10/2011
EP    3266481 A1   1/2018
(Continued)

OTHER PUBLICATIONS

Bhattacharyya et al., "RFID Tag Antenna Based Sensing: Does your Beverage Glass need a Refill?", RFID, 2010 IEEE International Conference on, IEEE, Piscataway, NJ, USA, Apr. 14, 2010 (Apr. 14, 2010), pp. 126-133, XP031677632, ISBN:978-1-4244-5742-7 p. 126 left column section I. Introduction I.1-14, p. 127 left col. I.1-11, p. 127 left column section III. Tag Antenna Based Sensing Principle I.1—p. 127 right col. I.12, p. 132 section IV. Conclusion I.1—p. 133. left column I.41.
(Continued)

*Primary Examiner* — Jason E Flick
(74) *Attorney, Agent, or Firm* — MASCHOFF BRENNAN

(57) ABSTRACT

Drip chamber detection assemblies for intravenous sets used with an infusion pump are provided. A drip chamber detection assembly includes a sensor coupled to a drip chamber. The sensor is positioned to generate signals related to the fluid level within the drip chamber. The signal data is transmitted to an infusion pump or a controller. A fluid level status or condition is determined and used for closed loop control of the infusion system, which generates an alarm and/or stops the infusion pump based on abnormal conditions. Methods of operating drip chamber detection assemblies are also provided.

14 Claims, 5 Drawing Sheets

(52) U.S. Cl.
CPC ............... *A61M 2205/3379* (2013.01); *A61M 2205/3592* (2013.01)

(58) Field of Classification Search
CPC .. A61M 2205/3592; A61M 2205/3306; A61M 5/1684; A61M 5/1411
See application file for complete search history.

(56) References Cited

U.S. PATENT DOCUMENTS

| | | |
|---|---|---|
| 2017/0216521 A1 | 8/2017 | Kolko et al. |
| 2018/0200431 A1 | 7/2018 | Nackaerts et al. |
| 2020/0114072 A1 | 4/2020 | Addiego et al. |

FOREIGN PATENT DOCUMENTS

| | | |
|---|---|---|
| JP | H0898885 A | 4/1996 |
| JP | 2007-298722 A | 11/2007 |
| JP | 2016-518875 A | 6/2016 |
| JP | 2020-028590 A | 2/2020 |

OTHER PUBLICATIONS

International Search Report and Written Opinion for Application No. PCT/US2021/032067, dated Aug. 19, 2021, 16 pages.
Japanese Office Action for Application No. 2022-572576, dated Feb. 5, 2025, 17 pages including translation.
Chinese Office Action for Application No. 202180038687.6, dated Mar. 27, 2025, 19 pages including translation.

\* cited by examiner

REAL TIME DRIP CHAMBER MONITOR

CROSS-REFERENCE TO RELATED APPLICATIONS

This patent application claims priority to U.S. Provisional Patent Application No. 63/030,817, entitled "REAL TIME DRIP CHAMBER MONITOR," and filed on May 27, 2020, the disclosure of which is hereby incorporated by reference in its entirety for all purposes.

TECHNICAL FIELD

The present disclosure generally relates to detecting unregulated flow conditions on an infusion pump, in particular a real time drip chamber monitor.

BACKGROUND

Intravenous (IV) sets are widely used in the medical field for gravity and infusion pump fluid delivery applications. Such IV sets typically have at least one flow control device, such as a drip chamber, a check valve and a roller clamp, for regulating the flow of fluid through the IV set. Proper operation of the IV set for an infusion pump requires being able to detect a free flow condition in the drip chamber and provide an alert and/or an action to remedy the condition. Typical solutions use an external optical sensor with the drip chamber or a camera vision system that images through the drip chamber wall and counts the drop formation to determine a free flow condition. However, these solutions are negatively affected by conditions such as discoloration in the drip chamber wall, cloudiness or condensation in the drip chamber and a small accumulated water drop on the drip chamber wall due to a dripping effect, which prevents the system from robustly identifying and counting drops in the drip chamber. For these reasons, it is desirable to provide a method and system that overcomes these limitations to accurately monitor the fluid level inside the drip chamber.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
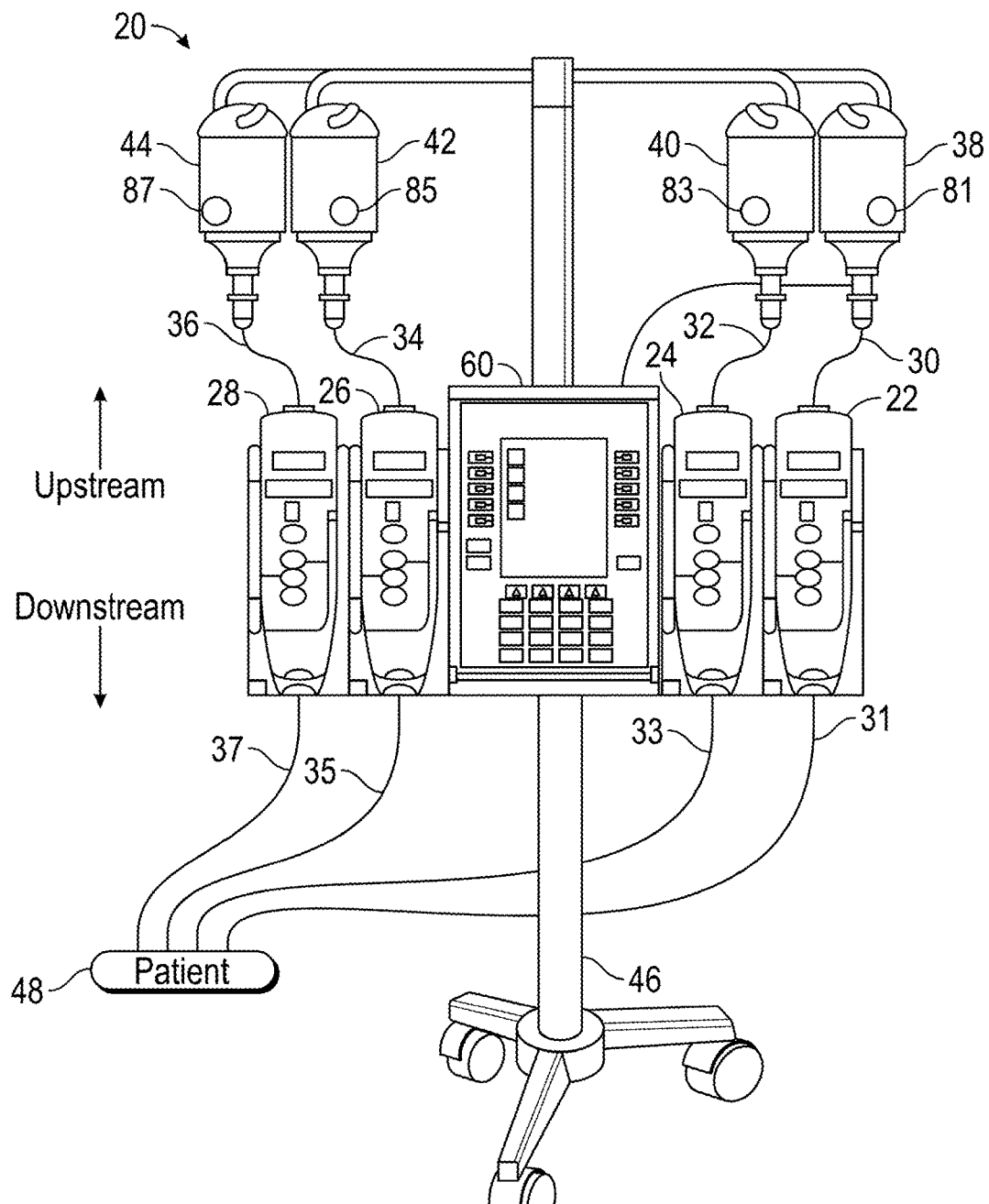
FIG. 1 depicts a front view of an example patient care system having four fluid infusion pumps, each of which is connected to a respective fluid supply for pumping the contents of the fluid supply to a patient.

As shown in FIG. 1, a patient care system 20 has a controller 60 and four infusion pumps 22, 24, 26, and 28, each of which is fluidly connected with an upstream fluid line 30, 32, 34, and 36, respectively. Each of the four infusion pumps 22, 24, 26, and 28 is also fluidly connected with a downstream fluid line 31, 33, 35, and 37, respectively. The fluid lines can be any type of fluid conduit, such as an IV administration set, through which fluid can flow through. It should be appreciated that any of a variety of pump mechanisms can be used including syringe pumps.

Fluid supplies 38, 40, 42, and 44, which may take various forms but in this case are shown as bottles, are inverted and suspended above the pumps. Fluid supplies may also take the form of bags or other types of containers including syringes. Both the patient care system 20 and the fluid supplies 38, 40, 42, and 44 are mounted to a roller stand, IV pole 46, table top, etc.

A separate infusion pump 22, 24, 26, and 28 is used to infuse each of the fluids of the fluid supplies into the patient. The infusion pumps are flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may include drugs or nutrients or other fluids.

Fluid supplies 38, 40, 42, and 44 are each coupled to an electronic data tag 81, 83, 85, and 87, respectively, or to an electronic transmitter. Any device or component associated with the infusion system may be equipped with an electronic data tag, reader, or transmitter.

Figure 2:
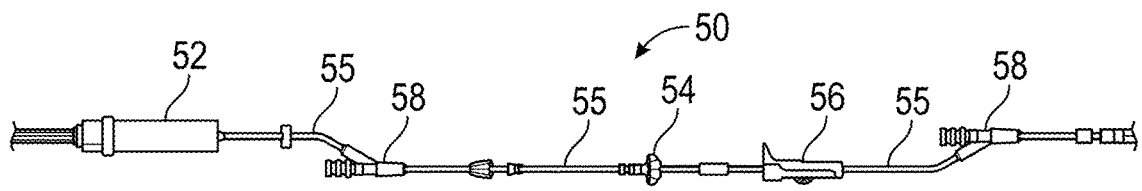
FIG. 2 depicts a schematic view of a typical assembled infusion set.

As shown in FIG. 2, a typical infusion set 50 may include a drip chamber 52, a check valve 54, a roller clamp 56 and Y-junctions 58, all connected together by tubing 55. A typical infusion set 50 can include additional infusion components and can be formed of any combination of components and the tubing 55. An external optical sensor or an external camera vision system may be used in conjunction with the drip chamber 52.

According to aspects of the disclosure, the subject technology is integrated into the IV set. This eliminates the need for external components to be added to the IV set and for the additional adjustment or calibration required to tune the external components to the drip chamber. Instead, the drip chamber is provided with an integral fluid level detection assembly that can be easily and efficiently coupled to an IV set.

Figure 3:
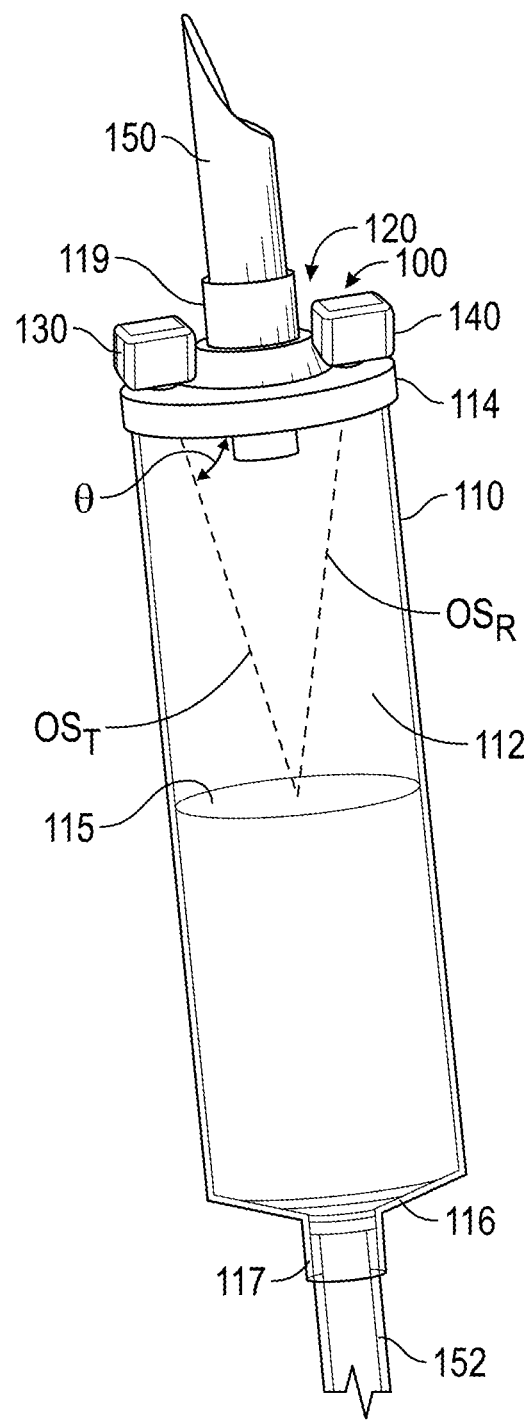
FIG. 3 depicts a perspective view of a drip chamber detection assembly, according to some aspects of the disclosure.
Figure 4:
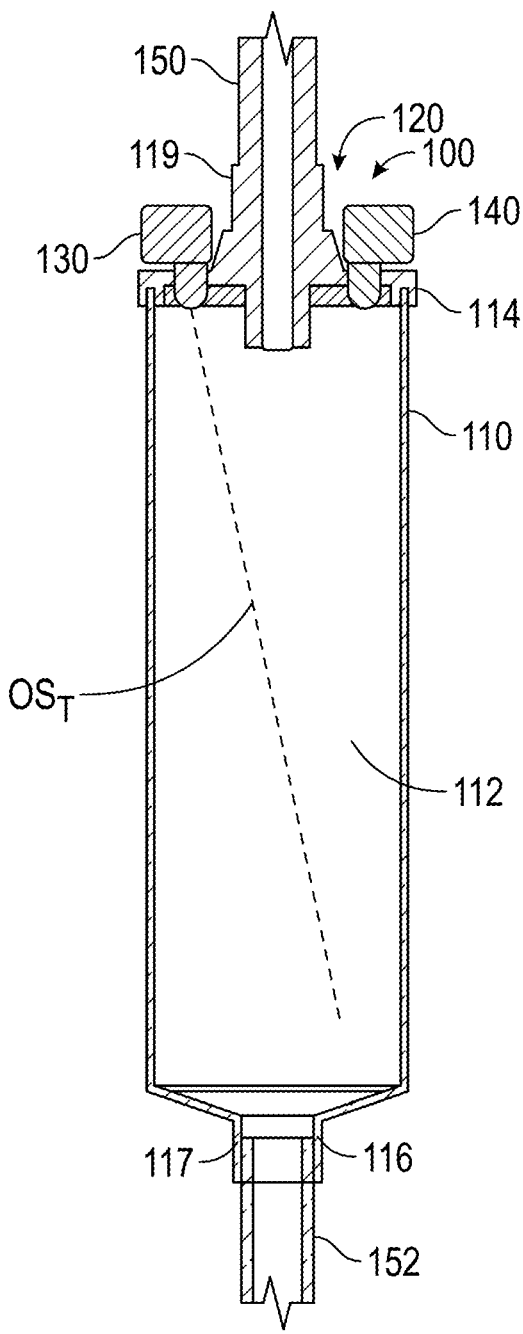
FIG. 4 depicts a cross-sectional front view of the drip chamber detection assembly of FIG. 3, according to some aspects of the disclosure.

Turning now to FIGS. 3 and 4, a drip chamber detection assembly 100 includes a drip chamber 110 having a chamber body 112, an inlet end 114 and an outlet end 116. The inlet end 114 includes an inlet connector 119 configured to couple with an inlet source 150 (e.g., tubing, spike) that may be coupled to a fluid source, such as a fluid bag or container (not shown). The outlet end 116 includes an outlet connector 117 configured to couple with an outlet receiver 152 (e.g., tubing) that may be coupled to another component in the IV set or to a patient.

The drip chamber detection assembly 100 includes an optical sensor 120 having a transmitter 130 and a receiver 140 (e.g. transmitter/receiver pair), each disposed on the inlet end 114 (e.g., top surface) of the chamber body 112. The transmitter 130 and receiver 140 are positioned to transmit an optical (e.g., light) signal $OS_T$ and receive an optical signal $OS_R$ at an angle relative to a fluid level 115 in the drip chamber 110. Thus, the transmitter 130/receiver 140 pair are focused at a point where the fluid level 115 will reflect the optical signal $OS_T$ transmitted from the transmitter 130 back as optical signal $OS_R$ to the receiver 140 when the chamber body 112 contains a fluid level 115, as shown in FIG. 3. When the chamber body 112 is empty as shown in FIG. 4, the optical signal $OS_T$ transmitted from the transmitter 130 has no fluid to reflect from and thus no optical signal $OS_R$ is received by the receiver 140.

The transmitter 130/receiver 140 pair positioning provides an angle θ looking down on the fluid level 115 and a resulting ripple perturbation formed due to fluid droplets striking the fluid level 115. By analyzing the reflected signal at the receiver 140 for a frequency of ripple perturbation and a rate of fluid level 115 change, a processor (e.g., controller 60) determines unregulated or free flow conditions within the IV set. Optical transmission and reception provides for accurately determining very low flow rates or drip rates within the chamber body 112. Data from the receiver 140 may be wired or wirelessly interfaced to an infusion pump (e.g., infusion pump 22, 24, 26, and 28) or a system processor (e.g., controller 60) to establish a closed loop control and to alert a user during abnormal flow conditions. By detecting a lack of a reflected signal at the receiver 140, the drip chamber detection assembly 100 may detect in real time if the fluid source has been emptied or is occluded, which information may be used in closed loop control of the system, such as automatically stopping the pump and/or generating an alert. As used herein, the term "real time" generally refers to a level of processing responsiveness that a user or system senses as sufficiently immediate for a subsequent process or determination to be timely made, or that enables the processor to keep up with some external process.

Figure 5:
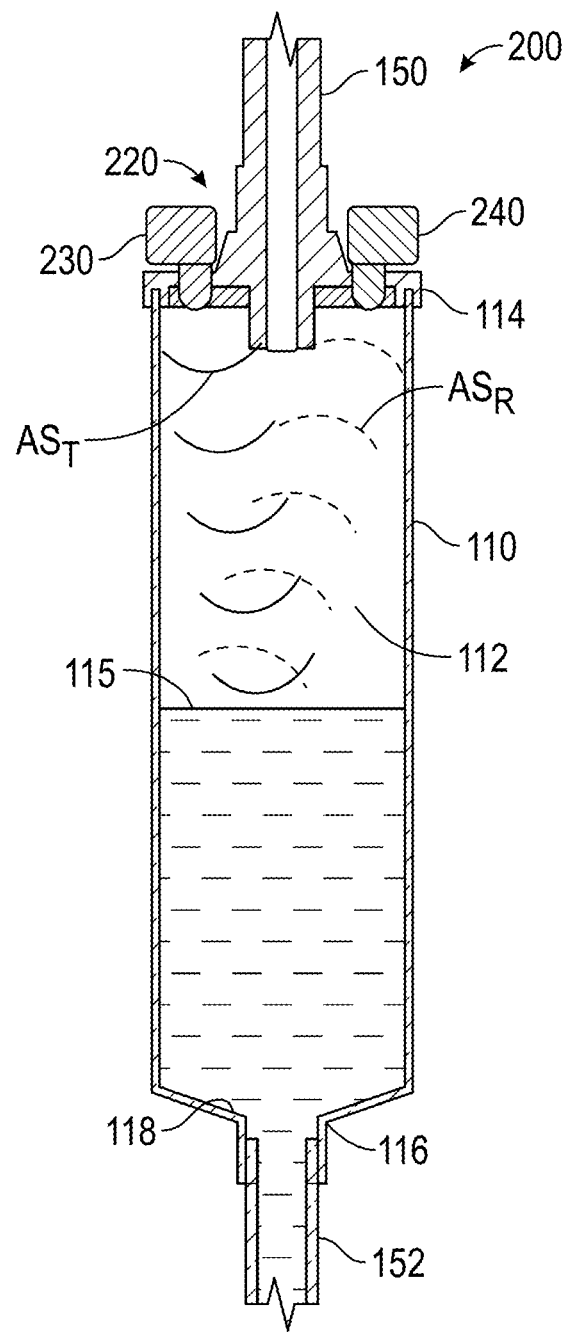
FIG. 5 depicts a cross-sectional front view of a drip chamber detection assembly with the drip chamber partially full, according to some aspects of the disclosure.
Figure 6:
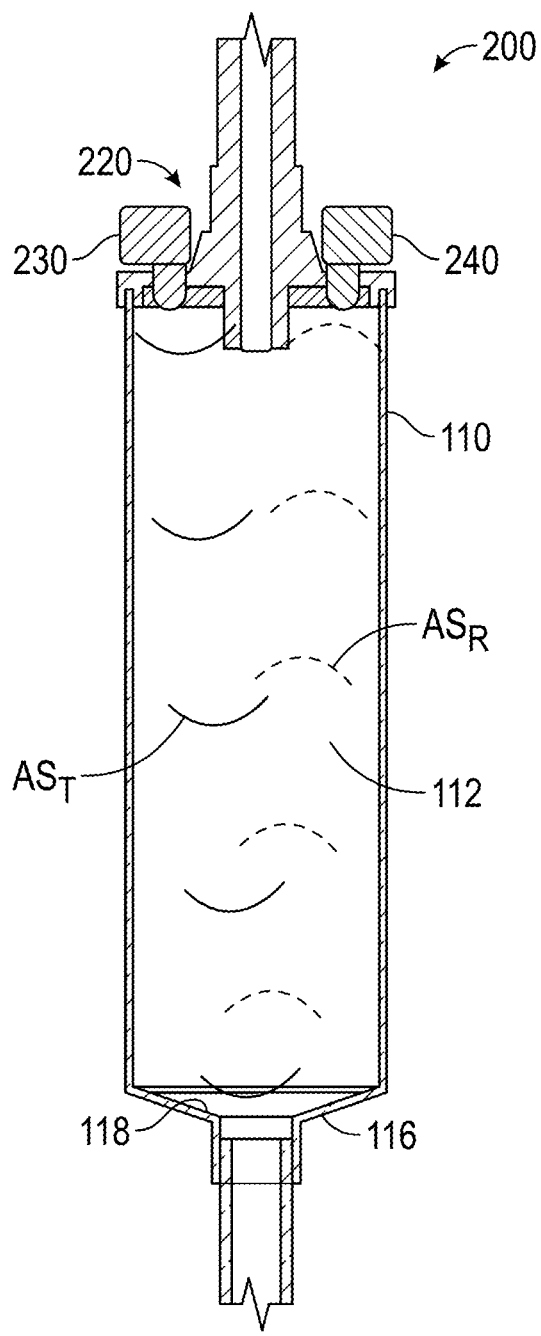
FIG. 6 depicts a cross-sectional front view of the drip chamber detection assembly of FIG. 5 with the drip chamber empty, according to some aspects of the disclosure.

Turning now to FIGS. 5 and 6, a drip chamber detection assembly 200 includes the drip chamber 110 discussed above. The drip chamber detection assembly 200 includes a sensor 220 having a transmitter 230 and a receiver 240 (e.g. transmitter/receiver pair), each disposed on the inlet end 114 (e.g., top surface) of the chamber body 112. The sensor 220 may be an acoustical sensor, such as an ultrasonic piezoelectric sensor, a time of flight sensor and the like. The transmitter 230 and receiver 240 are positioned to transmit an acoustic (e.g., sound) signal $AS_T$ and receive an acoustic signal $AS_R$ relative to the fluid level 115 in the drip chamber 110. Thus, the transmitter 230/receiver 240 pair are positioned where the fluid level 115 will reflect the acoustic signal transmitted from the transmitter 230 back to the receiver 240 when the chamber body 112 contains some level of fluid, as shown in FIG. 5. When the chamber body 112 is empty as shown in FIG. 6, the acoustic signal $AS_T$ transmitted from the transmitter 230 reflects from an inner surface 118 of the outlet end 116 and the acoustic signal $AS_R$ is received by the receiver 240. Here, the acoustic signal $AS_T$ travels the entire length of the chamber body 112 and thus the reflected acoustic signal $AS_R$ takes a longer period of time to reach the receiver 240.

The transmitter 230/receiver 240 pair positioning provides for bouncing the acoustic signal $AS_T$ off of the fluid level 115 or the inner surface 118 back as acoustic signal $AS_R$ to the receiver 240. By analyzing the time between transmission of the acoustic signal $AS_T$ from the transmitter 230 and reception of the acoustic signal $AS_R$ by the receiver 240 (e.g., time lag of signal), a processor (e.g., controller 60) measures and/or determines the level of fluid within the chamber body 112, which may be compared to known pump/IV set settings and/or previous fluid level measurements to determine a fluid flow rate. Here, the fluid level 115 inside the drip chamber 110 may be known in real time, providing the ability to determine a rate of change of the fluid level 115 and thus identify differences between normal and abnormal flow conditions.

Transmitting and receiving acoustic signals $AS_T$, $AS_R$ is not sensitive to lighting conditions and optical reflections, and detection of such signals provides for a very accurate fluid level detection in the chamber body 112. Data from the receiver 240 may be wired or wirelessly interfaced to an infusion pump (e.g., infusion pump 22, 24, 26, and 28) or a system processor (e.g., controller 60) to establish a closed loop control and to alert a user during abnormal flow conditions. By detecting a reflected acoustic signal $AS_R$ from the inner surface 118 at the receiver 240, the drip chamber detection assembly 200 may detect in real time if the fluid source has been emptied or is occluded, which information may be used in closed loop control of the system. The closed loop control may take actions based on the fluid source information, such as automatically stopping the pump and/or generating an alert.

A series of alarms may be provided to an interface and/or to a user based on varying levels of fluid in the chamber body 112. For example, an initial alarm may be provided when the fluid level drops below a specific level, and increasingly more urgent alarms may be generated as the fluid level continues to drop through successive threshold levels. Fluid level determinations may be used to provide information for pump operations. For example, if the chamber body 112 is determined to have no fluid level at all (e.g., chamber empty), a determination may be made that the fluid source (e.g., fluid supply 38, 40, 42, 44) is empty or that the pump (e.g., infusion pump 22, 24, 26, 28) is not operating normally during fill/delivery cycles (e.g., operating like a gravity IV set).

Figure 7:
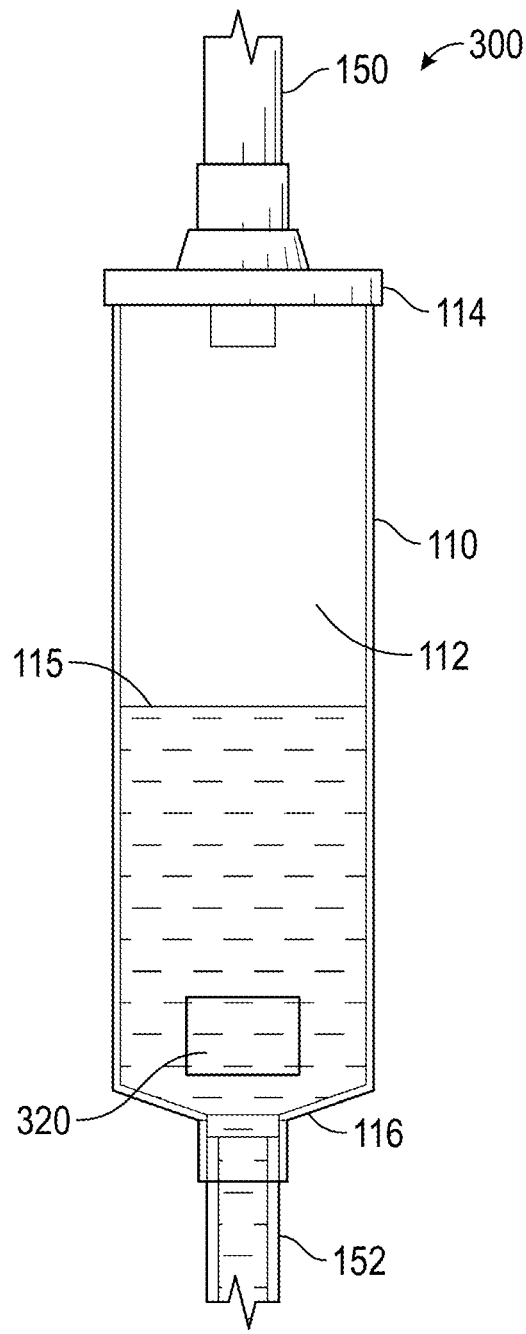
FIG. 7 depicts a front view of a drip chamber detection assembly with the drip chamber partially full, according to some aspects of the disclosure.
Figure 8:
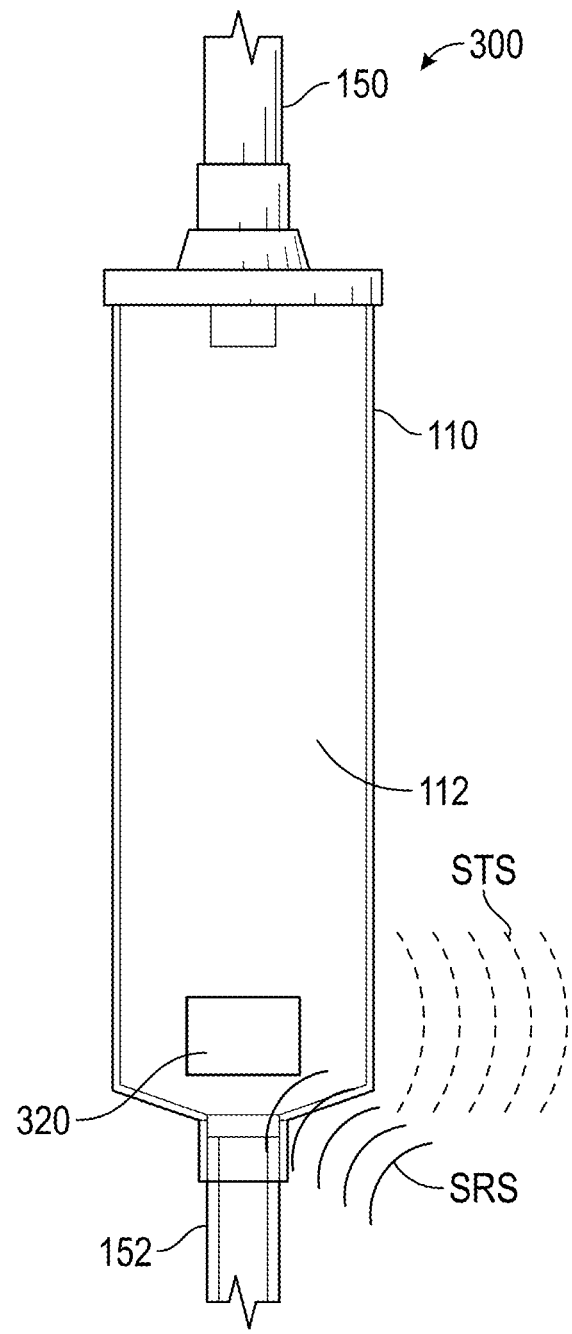
FIG. 8 depicts a front view of the drip chamber detection assembly of FIG. 7 with the drip chamber empty, according to some aspects of the disclosure.

Turning now to FIGS. 7 and 8, a drip chamber detection assembly 300 includes the drip chamber 110 discussed above. The drip chamber detection assembly 300 includes a sensor 320 disposed internally or externally on the chamber body 112. The sensor 320 may be a wireless sensor, a radio frequency (RF) sensor and the like, where the sensor 320 is not readable by a scanner read signal SRS or a sensor transmission signal STS from the sensor 320 is not able to pass out of the chamber body 112 when the sensor 320 is obscured by fluid level 115 in the chamber body 112, as shown in FIG. 7. However, the sensor 320 may reflect a scanner read signal SRS transmitted from a signal source/scanner or transmit a sensor transmission signal STS from the sensor 320 out of the drip chamber 110 when the chamber body 112 is empty, as shown in FIG. 8. The reflected scanner read signal SRS or transmitted sensor transmission signal STS signal may be received by a querying scanner or by any other reader.

For example, the sensor 320 may be a radio frequency identification (RFID) tag with an antenna where the degradation of RFID tag power characteristics is related to a change in a physical parameter. Thus, monitoring a change in RFID tag detection may be related to the state of an IV container (e.g., fluid supply 38, 40, 42, 44). In a full state, the background dielectric to the RFID tag is a fluid based medication. The main constituent of IV medications is water, and water is a polar dielectric that cancels out most of an incoming electric field from an RFID reader. Thus when the RFID tag is adjacent to fluid, the RFID tag will not be readable. However, in an empty state, the background dielectric to the RFID tag is air, which results in a readable state. Thus by observing a detection of the RFID tag, a change in state may be inferred of the drip chamber 110 from full to empty, and thus of the IV container (e.g., fluid supply 38, 40, 42, 44) from full to empty.

The sensor 320 may be positioned at any desired level of the chamber body 112. For example, the sensor 320 may be positioned at the bottom of the chamber body 112 as shown in FIG. 8. As another example, the sensor 320 may be positioned just below a threshold fluid level (e.g., fluid level 115) such that a signal is reflected or emitted from the sensor 320 when the fluid level drops below the sensor 320. As yet another example, multiple sensors 320 may be disposed at different positions on the chamber body 112 to provide a new reflected/emitted signal each time the fluid level drops below another one of the sensors 320. The one or more sensors 320 integrated into the IV set provide for monitoring the fluid level in the drip chamber 110 during normal conditions and fault conditions (e.g., fluid source empty, fluid inlet occluded).

Embodiments of the drip chamber detection assemblies described (e.g., assembly 100, assembly 200, or assembly 300) may include additional elements to support the detection features described. For example, a drip chamber detection assembly may include a power source to supply power to the elements included in the assembly. The power source may be an inductive power source to generate power from a wireless signal received from, for example, an infusion pump or an intravenous pole upon which the fluid source is hung. In some implementations, the power source may be a battery. In some implementations, the power may be received via a conductive path formed between the assembly and another device such as an infusion pump or intravenous pole upon which the fluid source is mounted. The conductive path may be formed on a portion of the administration set. Other examples of elements that can be included in the assembly include a microprocessor to coordinate all or portions of the detection process, a transceiver to communicate information to or from the assembly, a memory to store measurements or configurations for the detection processor, or an output element to provide a human perceivable output (e.g., audio, visual, haptic) indicating a status or state of the assembly or the infusion session including the assembly.

Example of closed loop control actions include actions to change the rate of infusion such as adjusting pumping rate or adjusting the height of the infusion fluid source. Other examples of closed loop control actions include disabling one or more functions of the infusion pump until the condition is adjusted or new information provided to the infusion pump (e.g., scanning of a new fluid source), dynamically updating a user interface based on the information received from a detection assembly, or causing playback of media content such as an audio file to provide verbal content to potentially correct a detected occlusion (e.g., a patient may inadvertently occlude an infusion line by, for example, the way their arm is laying, the audio file may provide a prompt to raise or move an arm).

The assemblies describe how acoustic or optical signals can be used to assess the fluid level within a drip chamber. The assessment may be based on measurement of the signals. In some implementations, the signals may be transformed to provide a measurement of the fluid level (e.g., signal strength n corresponds to x mL of fluid). The transformation may be dynamic based on characteristics of the infusion such as the fluid being infused, height of the fluid source, administration set configuration, or other parameter detectable proximate to the infusion pump. In some implementations, the assessment may be include time such as determining rates or trends. In such implementations, a single measured or transformed value may not, alone, cause a system response, but observation of a series of values (e.g., 3, 5, 10, or 100) may be used to detect infusion conditions (e.g., occlusion, empty container, etc.). The detection may include identifying correspondence between one or more measured or transformed values and a threshold. The detection threshold may be a static value stored by the system or a dynamic value generated based on, for example, characteristics of the infusion such as the fluid being infused, height of the fluid source, infusion pump flow rate, administration set configuration, or other parameter detectable proximate to the infusion pump.

Figure 9:
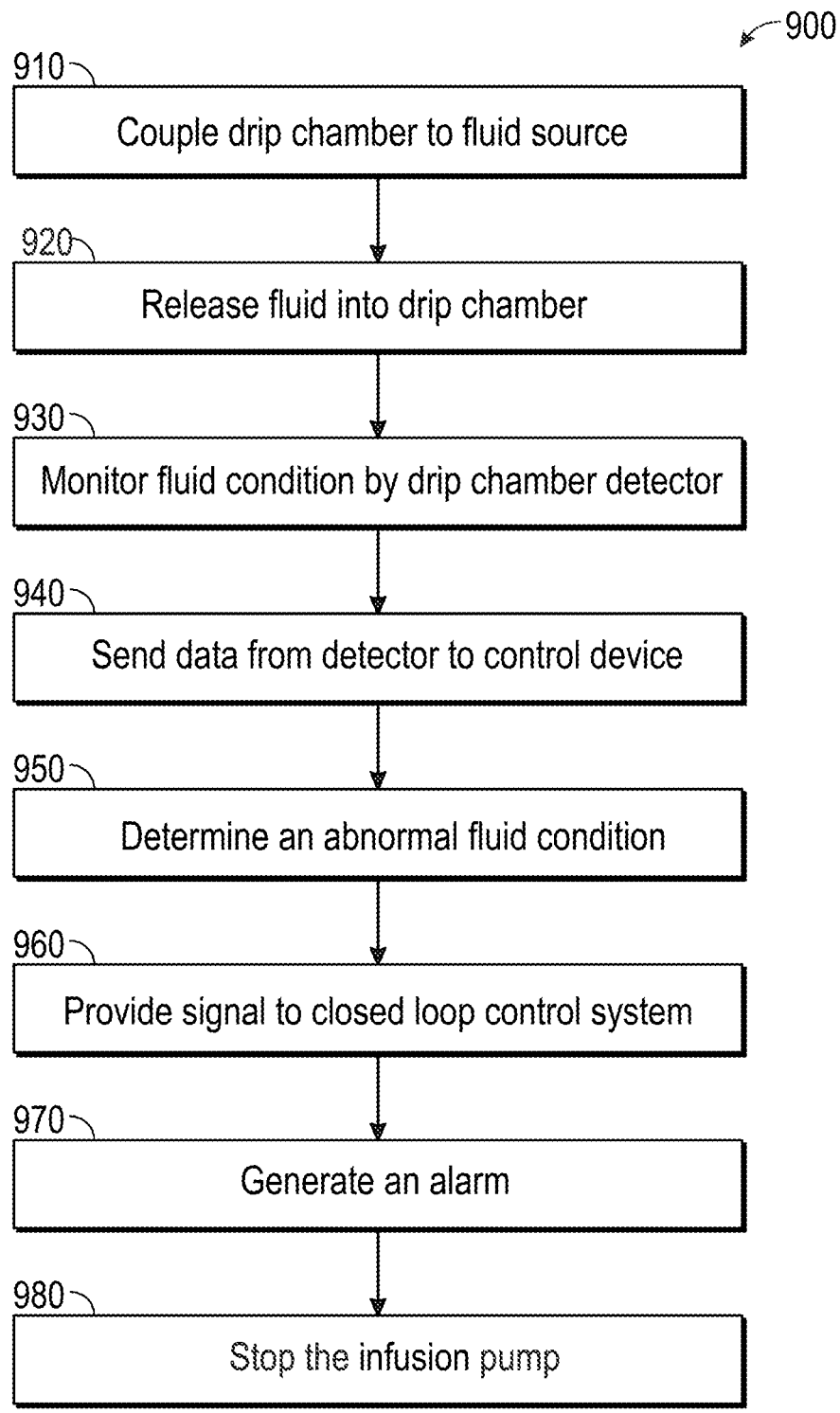
FIG. 9 depicts a flow diagram of a method of using a drip chamber detection assembly, according to some aspects of the disclosure.

FIG. 9 shows a method 900 of operating an IV set with a drip chamber detection assembly (e.g., drip chamber detection assembly 100, 200, 300). The method 900 may be performed or coordinated by one or more coordination devices such as the infusion pump, an infusion pump module, a patient care unit (PCU) associated with the infusion pump delivering the fluid, a server, an infusion pump controller, a microprocessor included in the detection assembly, or the like.

In step 910, a drip chamber (e.g., drip chamber 110) is fluidly coupled to a fluid container (e.g., fluid supply 38, 40, 42, 44). For example, tubing (e.g., tubing 55) may be coupled between the drip chamber (e.g., inlet connector 119) and the fluid container, or a spike may directly couple the drip chamber to the fluid container. Fluid is released from the fluid source into the drip chamber so that the drip chamber has a desired fluid level (e.g., fluid level 115), in step 920. In step 930, a fluid condition in the drip chamber is monitored by a drip chamber detector (e.g., drip chamber detection assembly 100, 200, 300) during operation of the IV set. For example, an optical signal (e.g., transmitter 130/receiver 140 pair), an ultrasonic/time of flight signal (e.g., transmitter 230/receiver 240 pair) or an RF signal (e.g., RFID tag 320) may be used to monitor the fluid level in the drip chamber.

In step 940, data from the drip chamber detector is wired or wirelessly sent to a control device (e.g., controller 60, infusion pump 22, 24, 26, 28). The received data is analyzed or measured to determine if an abnormal or undesired fluid condition is present (e.g., fluid source empty or occluded, incorrect fluid flow rate) in step 950. For example, an optical signal from a drip chamber detection assembly (e.g., drip chamber detection assembly 100) may be analyzed for a frequency of ripple perturbation and/or a rate of fluid level change, providing a real time indication that the fluid source has been emptied or is occluded. As another example, an ultrasonic signal from a drip chamber detection assembly (e.g., drip chamber detection assembly 200) may be analyzed to measure a fluid level in the drip chamber, which is then used to determine a fluid flow rate and identify differences between normal and abnormal flow conditions. In yet another example, an RFID signal from a drip chamber detection assembly (e.g., drip chamber detection assembly 300) may be analyzed to determine whether the drip chamber is empty, and thus in turn that the fluid source is empty or occluded.

In step 960, the determined condition is used for closed loop control of the infusion system. An alarm is generated by the closed loop control in step 970. For example, an alarm may be generated on a display of the infusion pump and/or on a user device. In step 980, the infusion pump is stopped by the closed loop control. For example, software of the infusion pump may automatically stop the pump upon generation or receipt of the determined condition. In another example, the infusion pump may be manually stopped by a user based on receiving the alarm from step 970.

In one or more embodiments of the disclosure, a drip chamber detection assembly includes a drip chamber. The drip chamber includes a chamber body, an inlet end having an inlet connector configured to couple with a fluid inlet source and an outlet end having an outlet connector configured to couple with an outlet receiver. The drip chamber detection assembly also includes a sensor integrally coupled to the drip chamber, the sensor configured to generate a signal within the chamber body, the signal indicating a fluid condition within the chamber body.

In aspects of the disclosure, the sensor is disposed on the inlet end of the drip chamber. In aspects of the disclosure, the sensor comprises a transmitter and a receiver configured as a transmitter/receiver pair. In aspects of the disclosure, the transmitter is an optical transmitter aligned to transmit an optical signal down to a fluid level in the chamber body, and wherein the receiver is an optical receiver aligned to receive the optical signal reflected up from the fluid level in the chamber body. In aspects of the disclosure, the optical signal is transmitted at a non-perpendicular angle from the inlet end, and wherein the reflected optical signal is received at a non-perpendicular angle to the inlet end.

In aspects of the disclosure, the chamber body is configured so that the optical signal is not reflected up to the optical receiver when the chamber body is empty of fluid. In aspects of the disclosure, the transmitter is an acoustic transmitter aligned to transmit an acoustic signal down to a fluid level in the chamber body, and wherein the receiver is an acoustic receiver aligned to receive the acoustic signal reflected up from the fluid level in the chamber body. In aspects of the disclosure, the acoustic receiver is aligned to receive the acoustic signal reflected up from an inner surface of the outlet end when the chamber body is empty of fluid. In aspects of the disclosure, the sensor is disposed on the chamber body of the drip chamber. In aspects of the disclosure, the sensor comprises a radio frequency identification (RFID) tag. In aspects of the disclosure, the RFID tag is configured to output a signal from the drip chamber when a fluid level in the chamber body does not occlude the RFID tag. In aspects of the disclosure, the sensor is configured to transmit fluid condition data to one of an infusion pump and a controller.

In one or more embodiments of the disclosure, an intravenous (IV) set includes a fluid source connector configured to be coupled to a fluid source, an IV tube and a drip chamber detection assembly. The drip chamber detection assembly includes a drip chamber body, an inlet end having an inlet connector coupled to the fluid source connector, an outlet end having an outlet connector coupled to the IV tube, and a sensor integrally coupled to one of the inlet end and the drip chamber body, the sensor configured to generate a signal within the drip chamber body, the signal indicating a fluid condition within the drip chamber body.

In aspects of the disclosure, the sensor is disposed on the inlet end, and wherein the sensor comprises a transmitter and a receiver configured as a transmitter/receiver pair. In aspects of the disclosure, the transmitter is aligned to transmit a signal down into the drip chamber body at a non-perpendicular angle from the inlet end, and wherein the receiver is aligned to receive the signal reflected up from within the drip chamber body at a non-perpendicular angle to the inlet end. In aspects of the disclosure, the transmitter is an optical transmitter aligned to transmit an optical signal down into the drip chamber body, wherein the receiver is an optical receiver aligned to receive the optical signal reflected up from a fluid when there is a fluid level in the drip chamber body, and wherein the drip chamber body is configured so that the optical signal is not reflected up to the optical receiver when the chamber body is empty of fluid.

In aspects of the disclosure, the transmitter is an acoustic transmitter aligned to transmit an acoustic signal down into the chamber body, and wherein the receiver is an acoustic receiver aligned to receive the acoustic signal reflected up from one of a fluid level in the chamber body and an inner surface of the outlet end when the chamber body is empty of fluid. In aspects of the disclosure, the sensor is disposed on the drip chamber body, and wherein the sensor is a radio frequency identification (RFID) tag configured to output a signal from the drip chamber body when a fluid level in the drip chamber body does not occlude the RFID tag.

In one or more embodiments of the disclosure, a method of operating an infusion pump with a drip chamber detection assembly includes coupling a drip chamber of an intravenous (IV) set to a fluid container, the drip chamber having a drip chamber detector, releasing fluid from the fluid container into the drip chamber, transmitting a signal from a transmitter of the drip chamber detector into a chamber body of the drip chamber, monitoring, by the drip chamber detector, a fluid condition in the chamber body during operation of the IV set based on the transmitted signal, transmitting fluid condition data from the drip chamber detector to a control device, determining, based on the fluid condition data, that an abnormal fluid condition is present in the drip chamber, and providing the determination of an abnormal fluid condition to a closed loop control system of the infusion pump.

In aspects of the disclosure, the method further includes generating, by the closed loop control system, an alarm and stopping, by the closed loop control system, the infusion pump.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, C, C++, web services, or rich site summary (RSS). In some embodiments, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML, document, fixed field message, comma separated message, JSON, a custom protocol, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A drip chamber detection assembly, comprising:
   a drip chamber comprising:
      a chamber body;
      an inlet end having an inlet connector configured to couple with a fluid inlet source; and
      an outlet end having an outlet connector configured to couple with an outlet receiver; and
   a sensor integrally coupled to the drip chamber and disposed on the inlet end of the drip chamber with a portion of the sensor extending into the chamber body, the sensor configured to generate a signal transmission and to receive a reflected signal completely within the chamber body, the signal indicating a fluid condition within the chamber body.

2. The drip chamber detection assembly of claim 1, wherein the sensor comprises a transmitter and a receiver configured as a transmitter/receiver pair.

3. The drip chamber detection assembly of claim 2, wherein the transmitter is an optical transmitter aligned to transmit an optical signal down to a fluid level in the chamber body, and wherein the receiver is an optical receiver aligned to receive the optical signal reflected up from the fluid level in the chamber body.

4. The drip chamber detection assembly of claim 3, wherein the optical signal is transmitted at a non-perpendicular angle from the inlet end, and wherein the reflected optical signal is received at a non-perpendicular angle to the inlet end.

5. The drip chamber detection assembly of claim 3, wherein the chamber body is configured so that the optical signal is not reflected up to the optical receiver when the chamber body is empty of fluid.

6. The drip chamber detection assembly of claim 2, wherein the transmitter is an acoustic transmitter aligned to transmit an acoustic signal down to a fluid level in the chamber body, and wherein the receiver is an acoustic receiver aligned to receive the acoustic signal reflected up from the fluid level in the chamber body.

7. The drip chamber detection assembly of claim 6, wherein the acoustic receiver is aligned to receive the acoustic signal reflected up from an inner surface of the outlet end when the chamber body is empty of fluid.

8. The drip chamber detection assembly of claim 1, wherein the sensor is configured to transmit fluid condition data to one of an infusion pump and a controller.

9. An intravenous (IV) set, comprising:
- a fluid source connector configured to be coupled to a fluid source;
- an IV tube; and
- a drip chamber detection assembly, the drip chamber detection assembly comprising:
  - a drip chamber body;
  - an inlet end having an inlet connector coupled to the fluid source connector;
  - an outlet end having an outlet connector coupled to the IV tube; and
  - a sensor integrally coupled to and disposed on an inlet end of the drip chamber body with a portion of the sensor extending into the chamber body, the sensor configured to generate a signal and receive a reflected signal only within the drip chamber body, the signal indicating a fluid condition within the drip chamber body.

10. The IV set of claim 9, wherein the sensor comprises a transmitter and a receiver configured as a transmitter/receiver pair.

11. The IV set of claim 10, wherein the transmitter is aligned to transmit a signal down into the drip chamber body at a non-perpendicular angle from the inlet end, and wherein the receiver is aligned to receive the signal reflected up from within the drip chamber body at a non-perpendicular angle to the inlet end.

12. The IV set of claim 10, wherein the transmitter is an optical transmitter aligned to transmit an optical signal down into the drip chamber body, wherein the receiver is an optical receiver aligned to receive the optical signal reflected up from a fluid when there is a fluid level in the drip chamber body, and wherein the drip chamber body is configured so that the optical signal is not reflected up to the optical receiver when the chamber body is empty of fluid.

13. The IV set of claim 10, wherein the transmitter is an acoustic transmitter aligned to transmit an acoustic signal down into the chamber body, and wherein the receiver is an acoustic receiver aligned to receive the acoustic signal reflected up from one of a fluid level in the chamber body and an inner surface of the outlet end when the chamber body is empty of fluid.

14. The drip chamber detection assembly of claim 2, wherein a portion of the transmitter extends into the chamber body and a portion of the receiver extends into the chamber body.

* * * * *